United States Patent
Georgopoulos

(10) Patent No.: US 10,561,639 B2
(45) Date of Patent: Feb. 18, 2020

(54) COMPOSITION COMPRISING A TNFR AGONIST AND AT LEAST ONE THIOREDOXIN INHIBITOR FOR USE IN THE TREATMENT OF CARCINOMA

(71) Applicant: UNIVERSITY OF HUDDERSFIELD, Queensgate, Huddersfield West Yorkshire (GB)

(72) Inventor: Nikolaos Georgopoulos, Huddersfield (GB)

(73) Assignee: University of Huddersfield, Huddersfield, West Yorkshire (GB)

( * ) Notice: Subject to any disclaimer, the term of this patent is extended or adjusted under 35 U.S.C. 154(b) by 83 days.

(21) Appl. No.: 14/765,724

(22) PCT Filed: Feb. 4, 2014

(86) PCT No.: PCT/GB2014/050305
§ 371 (c)(1),
(2) Date: Aug. 4, 2015

(87) PCT Pub. No.: WO2014/118578
PCT Pub. Date: Aug. 7, 2014

(65) Prior Publication Data
US 2015/0366844 A1 Dec. 24, 2015

(30) Foreign Application Priority Data

Feb. 4, 2013 (GB) .................................. 1301928.6
Jun. 11, 2013 (GB) .................................. 1310349.4

(51) Int. Cl.
| | | |
|---|---|---|
| *A61K 31/10* | (2006.01) | |
| *A61K 31/428* | (2006.01) | |
| *A61K 31/4164* | (2006.01) | |
| *A61K 38/17* | (2006.01) | |
| *A61K 38/19* | (2006.01) | |
| *A61K 39/395* | (2006.01) | |
| *C07K 14/435* | (2006.01) | |
| *C07K 14/705* | (2006.01) | |
| *C07K 14/715* | (2006.01) | |
| *C07K 16/24* | (2006.01) | |
| *C07K 16/18* | (2006.01) | |
| *C07K 16/28* | (2006.01) | |
| *A61K 39/00* | (2006.01) | |

(52) U.S. Cl.
CPC ........ *A61K 31/4164* (2013.01); *A61K 31/428* (2013.01); *A61K 38/191* (2013.01); *A61K 39/3955* (2013.01); *C07K 14/70575* (2013.01); *C07K 16/241* (2013.01); *C07K 16/2875* (2013.01); *A61K 31/10* (2013.01); *A61K 2039/505* (2013.01); *C07K 2317/75* (2013.01)

(58) Field of Classification Search
CPC ............ A61K 2300/00; A61K 39/3955; A61K 2039/505; A61K 31/404; A61K 38/191; A61K 38/08; A61K 39/00; A61K 39/395; A61K 38/177; A61K 38/10; A61K 36/16; C07K 2317/75; C07K 2319/00; C07K 16/241; C07K 14/705; C07K 14/435; C07K 7/00; C07K 9/00; C07K 14/00
See application file for complete search history.

(56) References Cited

U.S. PATENT DOCUMENTS

| | | | | |
|---|---|---|---|---|
| 6,312,691 | B1 * | 11/2001 | Browning ............ | A61K 38/191 |
| | | | | 424/130.1 |
| 7,300,774 | B1 * | 11/2007 | Kornbluth ............ | C07K 14/525 |
| | | | | 435/69.5 |
| 7,387,271 | B2 * | 6/2008 | Noelle ............... | A61K 31/4745 |
| | | | | 424/144.1 |

FOREIGN PATENT DOCUMENTS

WO    WO 03/04479 A1    1/2003

OTHER PUBLICATIONS

Ashkenazi, A. Targeting death and decoy receptors of the tumour-necrosis factor superfamily. Nature Rev Cancer 2(6): 420-430, 2002.*
Billiet et al. Thioredoxin-1 and its natural inhibitor, vitamin D2 up-regulated protein 1, are differentially regulated by PPARalpha in human macrophages. J Mol Biol 384: 564-576, 2008.*
Croft et al. Clinical targeting of the TNF and TNFR superfamilies. Nature Rev Drug Discov 12(2): 147-168, published online Jan. 21, 2013.*
Dal Piaz et al. Thioredoxin system modulation by plant and fungal secondary metabolites. Curr Med Chem 17: 479-494, 2010.*
Jones et al. Novel thioredoxin inhibitors paradoxically increase hypoxia-inducible factor-alpha expression but decrease functional transcriptional activity, DNA binding, and degradation. Clin Cancer Res 12(18): 5384-5394, 2006.*
Karlenius et al. Thioredoxin and cancer: a role for thioredoxin in all states of tumor oxygenation. Cancers 2: 209-232, 2010.*
Kirkpatrick et al. Mechanisms of inhibition of the thioredoxin growth factor system by antitumor 2-imidazolyl disulfides. Biochem Pharmacol 55: 987-994, 1998.*
Mahmood et al. The thioredoxin system as a therapeutic target in human health and disease. Antioxid Redox Signal 19: 1266-1303, 2013.*
Zhou et al. TXNIP (VDUP-1, TBP-2): a major redox regulator commonly suppressed in cancer by epigenetic mechanisms. Int J Biochem Cell Biol 43: 1668-1673, 2011.*
Albarbar et al. Regulation of cell fate by lymphotoxin (LT) receptor signalling: Functional differences and similarities of the LT system to other TNF superfamily (TNFSF) members. Cytokine GRowth Factor Rev 26: 659-671, 2015.*

(Continued)

*Primary Examiner* — Bridget E Bunner
(74) *Attorney, Agent, or Firm* — Gable Gotwals

(57) ABSTRACT

A composition for the treatment of cancerous cells. The composition including a combination of at least one tumor necrosis factor receptor (TNFR) agonist and at least one thioredoxin inhibitor. This combinatorial approach involves direct inhibition of the thioredoxin molecule (and not the enzyme of Trx reductase).

8 Claims, 6 Drawing Sheets

(56) References Cited

OTHER PUBLICATIONS

VanArsdale et al. Lymphotoxin-beta receptor signaling complex: role of tumor necrosis factor receptor-associated factor 3 recruitment in cell death and activation of nuclear factor KB. Proc Natl Acad Sci USA 94: 2460-2465, 1997.*

Freeman R E et al. Role of Thioredoxin-1 in Apoptosis Induction by Alpha-Tocopheryl Succinate and TNF-Related Apoptosis-Inducing Ligand in Mesothelioma Cells, Febs Letters, Elsevier, Amsterdam NL, FEBS Letters 580: 2671-2676, 2006.

T.Lin et al, 2-Tellurium-Bridged-Cyclodextrin, a Thioredoxin Reductase Inhibitor, Sentisizes Human Breast Cancer Cells to TRAIL-Induced Apoptosis Through DR5 Induction and NF-B Suppression, Carcinogenesis, Carcinogenesis 32(2): 154-167, 2010.

* cited by examiner

COMPOSITION COMPRISING A TNFR AGONIST AND AT LEAST ONE THIOREDOXIN INHIBITOR FOR USE IN THE TREATMENT OF CARCINOMA

CROSS-REFERENCE TO RELATED APPLICATIONS

This application is the United States National Phase of Patent Application No. PCT/GB2014/050305 filed 4 Feb. 2014, which claims priority to British Patent Application Nos. 1301928.6 filed 4 Feb. 2013 and 1310349.4 filed 11 Jun. 2013, each of which is incorporated herein by reference.

BACKGROUND OF THE INVENTION

The present invention relates to the production and use of a composition suitable for use in carcinoma therapy.

Although the following description refers exclusively to the Thioredoxin family of proteins, the person skilled in the art will appreciate that the present invention could also be used for other proteins and protein families that are involved in Reactive Oxygen Species (ROS) signalling pathways.

The Tumour Necrosis Factor receptor (TNFR) family, commonly known as "death receptors", provides a popular therapeutic avenue for anti-cancer therapy. Activation by binding and/or or cross-linking of the classical death receptors, such as TNF-RI, Fas and TRAIL-R, and non-classical TNFRs, such as CD40 and Lymphotoxin-receptor (LT-R), by their cognate ligands can induce apoptosis in carcinoma cells of various tissue origins.

However, it has been found previously that recombinant soluble trimeric TNFR agonists are inefficient at killing tumour cells as they do not appear to cross-link TNFRs sufficiently to engage intracellular apoptotic signalling pathways. As such, these ligands are only cytostatic and can only be strongly pro-apoptotic in combination with pharmacological inhibitors of protein synthesis, which are highly toxic to epithelial cells. By contrast, highly cross-linked TNFR ligands, either multimeric aggregates of agonists or cell surface (membrane-presented)-delivered ligands can induce extensive killing in carcinoma cells.

However, in some cases such highly cross-linked agonists are non-specific to tumour cells and they have demonstrated severe cytotoxicity in normal cells (TNF-Related Apoptosis Inducing Ligand (TRAIL)-R agonists, for example).

One exception to this in the TNFR family members is CD40, which is uniquely tumour specific, as it has been shown to induce extensive apoptosis in malignant cells but not normal epithelial cells. However, despite this particular ability, CD40-killing requires extensive receptor cross-linking, and therefore requires cell surface-delivered ligand delivery for its activation, which due to the insolubility in aqueous systems of the surface immobilised ligand, presents a serious therapeutic obstacle.

Lin et al., 2010, Carcinogenesis, 32: 154 discloses the use of 2-tellerium-bridged beta-cyclodextrin (TeCD) compounds in combination with TRAIL ligand to kill TRAIL-resistant tumour cells by inhibition of the Trx reductase enzyme along with other enzymes (relating to the Gluta-thione pathway) that affect detoxifying mechanisms relating to NF-kappaB. As such this paper teaches methods to sensitize tumour cells to TRAIL by targeting (inhibiting) protective, NF-kappaB transcription factor-driven anti-apoptotic pathways. A major problem with such an approach is that targeting an enzyme poses the additional risk of tumours developing resistance to such inhibitors by mutations, as is the case with several drugs already used, such as tyrosine kinase inhibitors.

BRIEF SUMMARY OF THE INVENTION

It is therefore an aim of the present invention to provide an improved composition that addresses the abovementioned problems.

It is a further aim of the present invention to provide a composition as a method of treating cancerous cells and/or tumours.

It is a yet further aim of the present invention to provide a means of increasing the pro-apoptotic ability of soluble TNFR agonists by combinatorial approaches that will optimally exploit their cytotoxic potential.

According to a first aspect of the invention there is provided a composition for the treatment of cancerous cells, said composition including a combination of at least one Tumor Necrosis Factor receptor (TNFR) agonist and at least one thioredoxin inhibitor.

This combinatorial approach involves direct inhibition of the Thioredoxin molecule (and not the enzyme of Trx reductase). Typically thioredoxin is inhibited by the reaction of the thioredoxin molecule with at least one other compound. Further typically the reaction alters the structure of the thioredoxin molecule.

The present invention therefore has the advantage that the combinatorial treatment of a TNFR agonist with a thioredoxin inhibitor engages a pathway that is equivalent to that triggered by insoluble highly cross-linked TNFR agonists, both functionally (intracellular signalling mechanisms) and in terms or pro-apoptotic potential. This combinatorial approach achieves the maximal, pro-apoptotic, TNFR agonist-driven signal and alleviates the need for using complex and insoluble signal delivery strategies.

Preferably, said TNFR agonist is soluble in aqueous media and/or bulk phase solutions. Typically the TNFR agonist is a ligand for one or more TNFR.

In one embodiment the TNFR agonist is a non-classical agonist. Typically classical death receptors are those receptors the cytoplasmic (intracellular) tail of which contains a death domain via which the receptor transmits its apoptotic signals (for example the classical, FADD/TRADD, caspase-8 and caspase-3 pathway). Further non-classical receptors induce apoptosis without engaging the same downstream signalling pathway Typically the TNFR agonist is any one or any combination of recombinant soluble trimeric ligands, recombinant soluble multimeric ligands, agonistic TNFR antibodies (alone or cross-linked using appropriate immunoglobulins), cell surface-presented or membrane-presented TNFR agonists (usually trimeric ligands or antibodies), TNFR agonists on nanoparticles, TNFR ligands delivered by viral expression vectors.

In one embodiment the TNFRs include CD40, Lymphotoxin receptor, herpesvirus entry mediator (HVEM), Fas, TNF-receptors I & II, TRAIL-receptors, DcR3, TRAMP, TWEAK, RANK, BAFF-receptor, BCMA, CD30, OX40, GITR.

In one embodiment the TNFR agonist is at least one Lymphotoxin beta receptor (LTbR) agonist. Typically the TNFR is a humanized tetravalent LTBR agonistic antibody.

Preferably the TNFR is CD40.

In one embodiment, said thioredoxin inhibitor is a redox inhibitor. Typically the thioredoxin inhibitor is an inhibitor of the thioredoxin-1 pathway. Further typically the thioredoxin inhibitor includes any one or any combination of 2-[(1-Methylpropyl)dithio]-1H-imidazole (PX-12), PMX464, analogues of the aforementioned and/or the like.

Typically the TNFR agonist and/or thioredoxin inhibitor are used in pharmacologically significant amounts. Further typically using this combinatorial approach relatively smaller doses of PX-12 are used of around 2 µg/mL.

PX-12 is a Trx-specific inhibitor, and functions as an irreversible inhibitor by binding to the amino acid Cys73 on the Trx protein. Typically the concentration of PX-12 is equal to or less than 2 µg/mL. This compares favourably with the much higher (10 to 25 µg/mL) doses required for conventional PX-12 treatment to obtain cytotoxicity.

In a second aspect of the invention a first composition is used as a medicament for the treatment of carcinoma in humans and/or animals, said composition including a combination of at least one Tumor Necrosis Factor receptor (TNFR) agonist and at least one thioredoxin inhibitor.

Typically pharmaceutically acceptable salts of the Tumor Necrosis Factor receptor (TNFR) agonist and/or the thioredoxin inhibitor are used.

A method of treating human and/or animal carcinoma cells using a first composition, said composition including a combination of at least one Tumor Necrosis Factor receptor (TNFR) agonist and at least one thioredoxin inhibitor.

BRIEF DESCRIPTION OF THE DRAWINGS

Embodiments of the present invention will now be described with reference to the accompanying figures, wherein.

DETAILED DESCRIPTION

Figure 1:
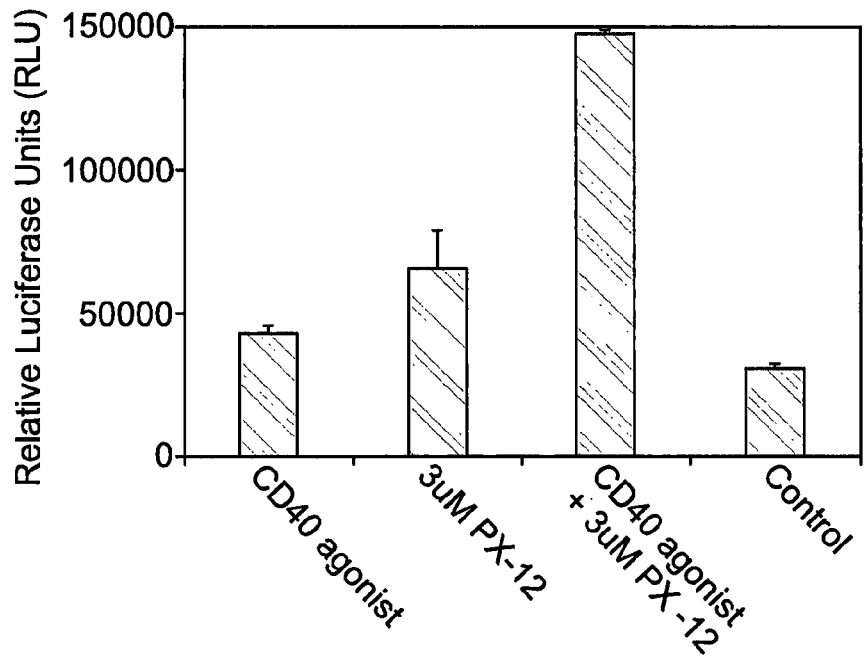
FIG. 1 shows a graph comparing apoptosis in carcinoma cells treated with soluble CD40 agonist (agonistic antibody G28-5), a thioredoxin inhibitor (PX-12), a combination of G28-5 and PX-12, and untreated (Control) cells.

The present invention combines the use of a TNFR agonist and thioredoxin (Trx) inhibitor in order to induce cytotoxic responses in carcinoma cells for anticancer therapy in solid tumours.

PX-12 is a Trx-specific inhibitor, not a TrxR (Trx reductase) inhibitor, and functions as an irreversible inhibitor by binding to the amino acid Cys73 on the Trx protein.

Although the TNFR agonist was used at biologically functional concentrations (induced intracellular ROS levels), it caused no or little apoptosis. However, when combined with Trx inhibitor that was provided at concentrations that induced no or little cell death (sub-cytotoxic), there was extensive induction of apoptosis.

Our biological studies have shown that the combinatorial treatment disclosed herein engages a pathway that is equivalent to that triggered by highly cross-linked TNFR agonist both functionally (intracellular signalling mechanisms) and in terms of pro-apoptotic potential. Therefore this combinatorial approach achieves the maximal, pro-apoptotic, TNFR agonist-driven signal and negates complex signal delivery strategies.

Increasing evidence suggests that Reactive Oxygen Species (ROS) molecules progressively accumulate in carcinoma cells due to chronic oncogenic stimulation and increased metabolic activity. ROS appear to be important in supporting cell growth in the tumour microenvironment as a response of cancer cells to cellular stress and they also enhance chronic genetic instability. However, the increased basal ROS levels can render tumour cells more susceptible to apoptosis. Pro-apoptotic signals triggered by members of the TNFR family, such as CD40, utilise a sustained ROS activation to induce cell death. Such signals increase the levels of intracellular ROS above a certain biological threshold, which appears to shift the signalling balance towards induction of apoptosis rather than cell growth.

The best characterised intracellular signalling pathway that links increased ROS levels and induction of cell death is that of the Apoptosis Signal-regulating Kinase-1 (ASK-1). ASK-1 can induce an intracellular signalling cascade that activates Jun-N-terminal kinase (JNK) which in turns promotes mitochondrial-mediated apoptosis. Such is the importance and potency of this pathway for inducing cell death, that under physiological circumstances, ASK-1 is kept inactivated. Members of the Thioredoxin (Trx) family of proteins can function as effective antioxidants. The best characterised member of the family, Thioredoxin-1, has been shown to be responsible for inhibiting ASK-1 activity by physically binding to the ASK-1, thus keeping the kinase inactivated under physiological conditions. Yet, upon sustained increase of ROS levels, for instance following CD40 activation, Trx becomes oxidised and no longer binds to ASK-1, which allows ASK-1 to be released and induce cell apoptosis.

Although increased basal ROS levels provide a growth advantage, it is necessary for tumour cells to ensure that they are protected against ROS-mediated toxicity. One of the mechanisms that tumour cells develop to defend against oxidative stress is the induction of protective mechanisms against ROS-mediated apoptosis. In particular, it appears that often tumour cells can up-regulate Trx family members in an attempt to keep ASK-1 inhibited.

Therefore, treatment of carcinoma cells with regimens that a) shift the balance of intracellular ROS over the cytoprotective threshold and b) block Trx-mediated, anti-apoptotic cytoprotection provide a novel route that can be exploited for therapeutic purposes.

Referring firstly to FIG. 1 where comparative results are shown from Bladder carcinoma cells (EJ) treated with soluble CD40 agonist (agonistic antibody G28-5), the indicated concentration of Trx inhibitor (PX-12), or their combination and results compared to untreated (Control) cells. Apoptosis was assessed 48 hours later using the Cytotox-Glo assay (Promega). Raw data (relative luminescence units) are shown and results are representative of three independent experiments in which six technical replicates were carried out for each condition.

The results indicate that although soluble CD40 agonist and the Trx inhibitor (concentration selected that showed minimal cytotoxicity following pre-titration experiments) alone showed no or little cytotoxicity, respectively, in combination they induced extensive apoptosis in carcinoma cells.

Figure 2:
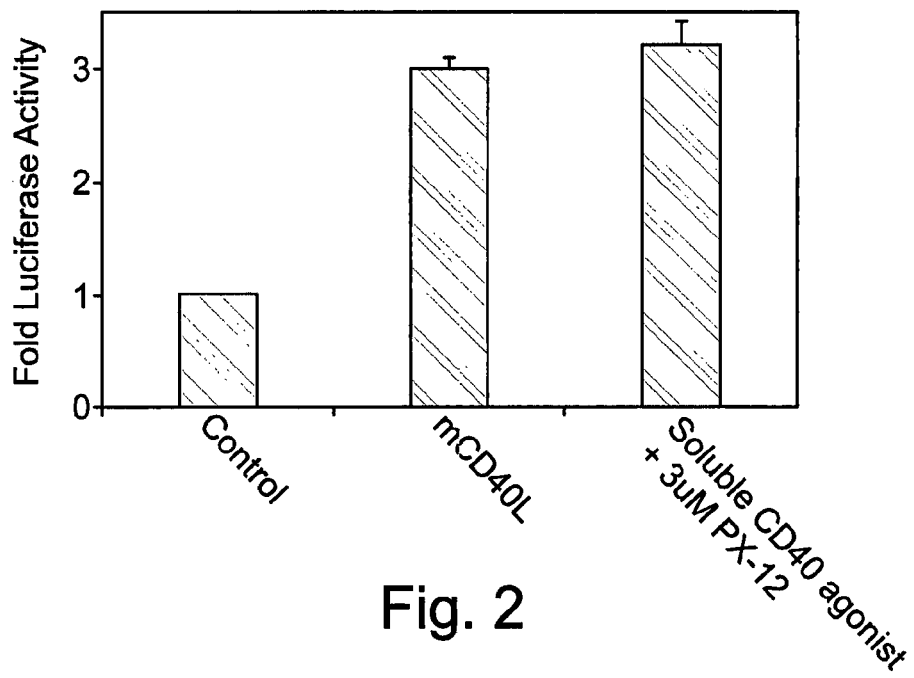
FIG. 2 shows a graph comparing apoptosis in carcinoma cells treated with a membrane bound CD40 agonist mCD40L, (agonistic antibody G28-5), soluble agonist (agonistic antibody G28-5) in combination with thioredoxin inhibitor (PX-12), and untreated (Control) cells.

FIG. 2 shows results wherein to induce CD40-mediated apoptosis, bladder carcinoma cells (EJ) were treated wither with membrane CD40 ligand, mCD40L (by co-culture with growth-arrested third-party cells expressing mCD40L) or with soluble agonist (agonistic antibody G28-5) in combination with Trx inhibitor (PX-12). Apoptosis was assessed 48 hours later using the Cytotox-Glo assay (Promega). Results are expressed as relative luciferase in comparison to negative controls and are representative of four independent experiments in which six technical replicates were carried out for each condition.

Figure 3:
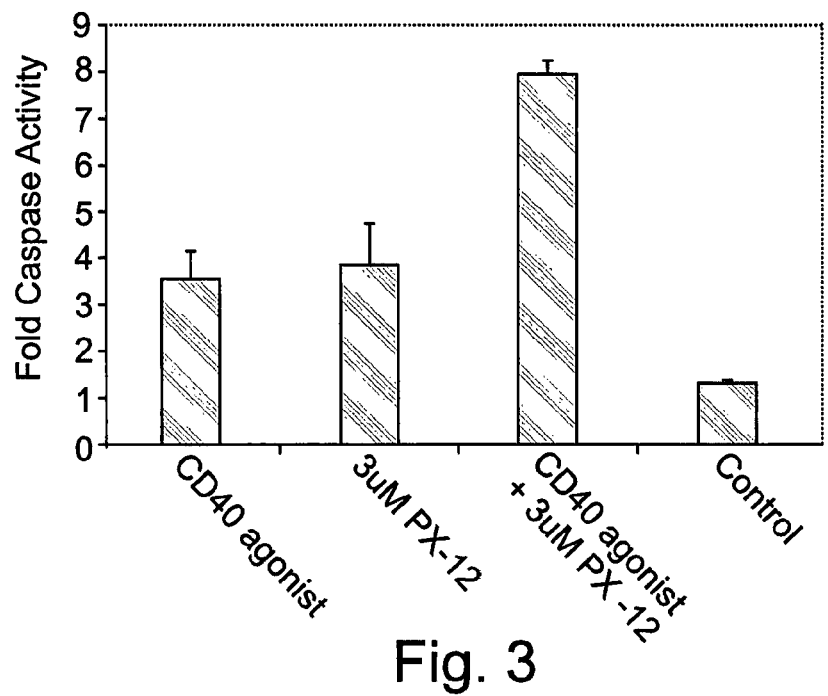
FIG. 3 shows a graph comparing apoptosis in carcinoma cells treated with a soluble CD40 agonist (agonistic antibody G28-5), 3 µM of thioredoxin inhibitor (PX-12), combination of CD40 agonist (agonistic antibody G28-5) and 3 µM of thioredoxin inhibitor (PX-12), and untreated (Control) cells.

FIG. 3 shows results wherein colorectal carcinoma cells (HCT116) were treated with soluble CD40 agonist (agonistic antibody G28-5), the indicated concentration of Trx inhibitor (PX-12), or their combination and results were compared to untreated (Control) cells. Apoptosis was assessed on the basis of caspase activity detection after 24 hours of treatment using the Sensolyte (Anaspec) assay (Cambridge Biosciences). Results are expressed as relative fluorescence (relative caspase activity) in comparison to negative controls and are representative of two independent experiments in which six technical replicates were carried out for each condition.

The results indicate that soluble CD40 agonist and the Trx inhibitor alone showed some cytotoxicity in comparison to controls as evidenced by the induction of caspase activation. However, in combination, soluble agonist and Trx inhibitor induced extensive apoptosis in carcinoma cells.

Figure 4:
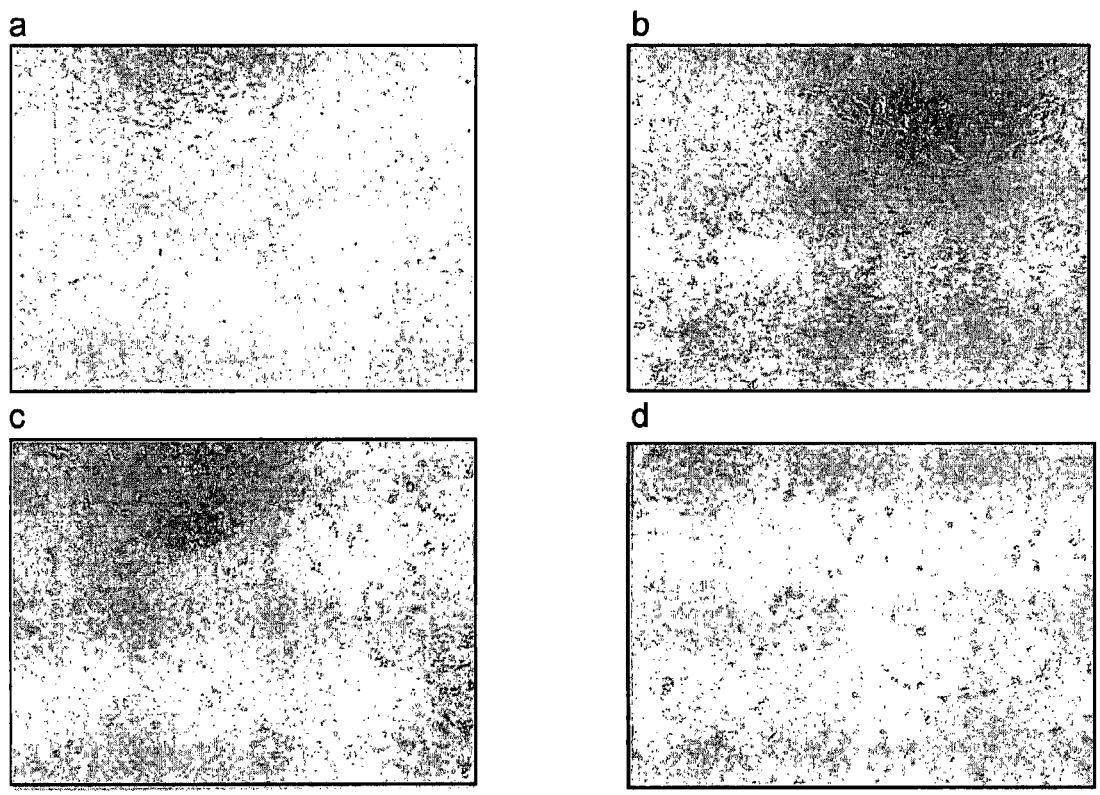
FIGS. 4a-4d show phase contact images of carcinoma cells with healthy control cells (i.e. vehicle alone), thioredoxin inhibitor PX-12 alone, PX-12+agonistic anti-CD40 antibody G28-5 and PX-12+cross-linked recombinant MegaCD40L™ preparation respectively.

FIG. 4 shows colorectal carcinoma cells HCT116 treated with: a) vehicle alone (i.e. control, healthy cells), b) Trx inhibitor PX-12 alone, c) PX-12+agonistic anti-CD40 antibody G28-5 and d) PX-12+cross-linked recombinant MegaCD40L™ preparation (Enzo Life Sciences).

Control cultures treated with agonistic anti-CD40 antibody G28-5 alone or cross-linked recombinant MegaCD40L™ preparation showed no signs of loss of viability and were similar to panel "a" (not shown).

Phase contract images were taken at ×100 magnification to assess visible signs of growth inhibition and apoptosis in 96 well plates.

The results are in agreement with the apoptosis detection assays (FIG. 3), showing that only the combination of soluble agonists and Trx inhibitor induced detectable, extensive apoptosis in carcinoma cells.

The results indicate that combinatorial treatment of carcinoma cells with soluble agonist and Trx inhibitor induces the same level of apoptosis as the highly cross-linked membrane-presented CD40 agonist (mCD40L).

The aforementioned results were obtained using the following:

Cell Culture:

Carcinoma cell lines EJ and HCT116 (obtained from the European Collection of Cell Cultures, ECACC) were maintained in a 50:50 (v/v) mixture of Dulbecco's Modified Eagle Medium (DMEM, Sigma) and Roswell Park Memorial Institute 1640 (RPMI, Sigma) (DR), supplemented with 5% Fetal calf serum (FCS, Biosera) and 1% (2 mM) L-Glutamine (Sigma). Cells were incubated at 37° C. in a humidified atmosphere of 5% CO2 in air. For routine passaging and experimentation, cell monolayers were incubated in 0.1% (w/v) in Ethylenediaminetetra-acetic acid disodium salt (EDTA) in PBS for 5 minutes at 37° C. to chelate calcium and promote dissociation. Cells were then incubated in 0.5 mL of Hank's buffered salt solution (HBSS; Invitrogen) containing 0.25% (w/v) trypsin and 0.02% (w/v) EDTA for <1 minute at 37° C. Cells were removed with a 10 mL suspension of DR 5% and counted in single cell suspension using an "improved Neubauer" haemocytometer (VWR).

Apoptosis Detection Assays:

EJ and HT116 cells were seeded into white 96-well plates (at 8×103 and 6×103 cells per well, respectively) and left incubated overnight. The next day cells were pre-treated with the indicated concentration of PX-12 in DR 5% medium for 1 hour. Post treatment with PX-12, the agonistic anti-CD40 mAb G28-5 or MegaCD40L™ preparation (Enzo) was added at a final concentration of 10 ug/mL or 10 ug/mL, respectively, in medium. Cells were then incubated for 48 hours before assessing cell death using the CytoTox-Glo™ cell death detection assay (according to the manufacturer's instructions) on a FLUOstar™ OPTIMA (BMG Labtech) plate reader. Alternatively, after 24 or 48 hours caspase activity was determined using the SensoLyte® Homogenous AFC Caspase-3/7 Assay Kit (Anaspec). After addition of the substrate cells were left overnight before relative fluorescence was measured (using excitation 355 and emission 520 filters) on a FLUOstar™ OPTIMA (BMG Labtech) reader.

Microscopic Examination:

Following treatment of HCT116 cells seeded in transparent 96-well plates for the indicated time periods and treated with the indicated concentrations of agonists and PX-12 (as described above), morphological changes associated with growth inhibition/apoptosis were visualized by phase contrast microscopy on an EVOS XL Core digital inverted microscope (Peqlab) at ×200 magnification.

Figure 5:
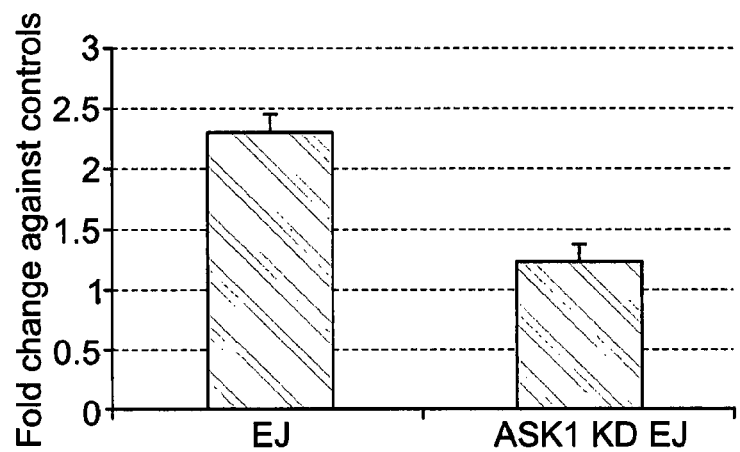
FIG. 5 shows a graph comparing apoptosis in bladder cancer cells and ASK-1 protein knock out derivatives expressing ASK-1 shRNA after treatment with mCD40L.
Figures 6A, 6B:
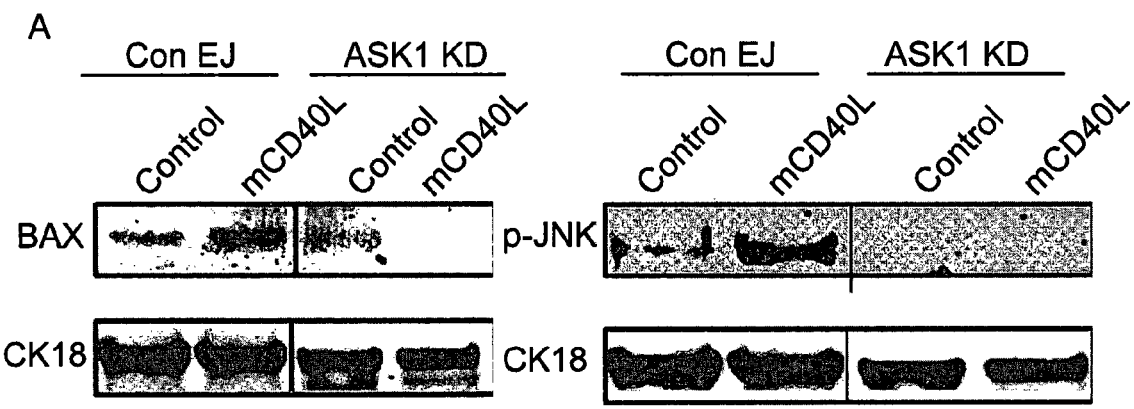
FIGS. 6a and 6b show images of the electrophoresis results of apoptosis in bladder cancer cells and ASK-1 protein knock out derivatives expressing ASK-1 shRNA after treatment with mCD40L.

FIG. 5 shows a graph of the comparison of bladder cancer EJ cells and ASK-1 protein knock-out EJ cell derivatives ('S18') expressing ASK-1 shRNA following retroviral transduction. The cells were treated with mCD40L and apoptosis was assessed 48 hours later using the Cytotox-Glo assay (Promega) and by measuring levels of phospho-JNK and Bax using immune-blotting. The images from the blotting can be seen in FIGS. 6a and 6b.

This test demonstrates the importance of the ROS-ASK1 signalling pathway in cell death through the lack of p-JNK and Bax induction in cells with ASK-1 knockdown and the inhibition of apoptosis due to loss of ASK-1 assessed using Cytotox Glo.

Figure 7:
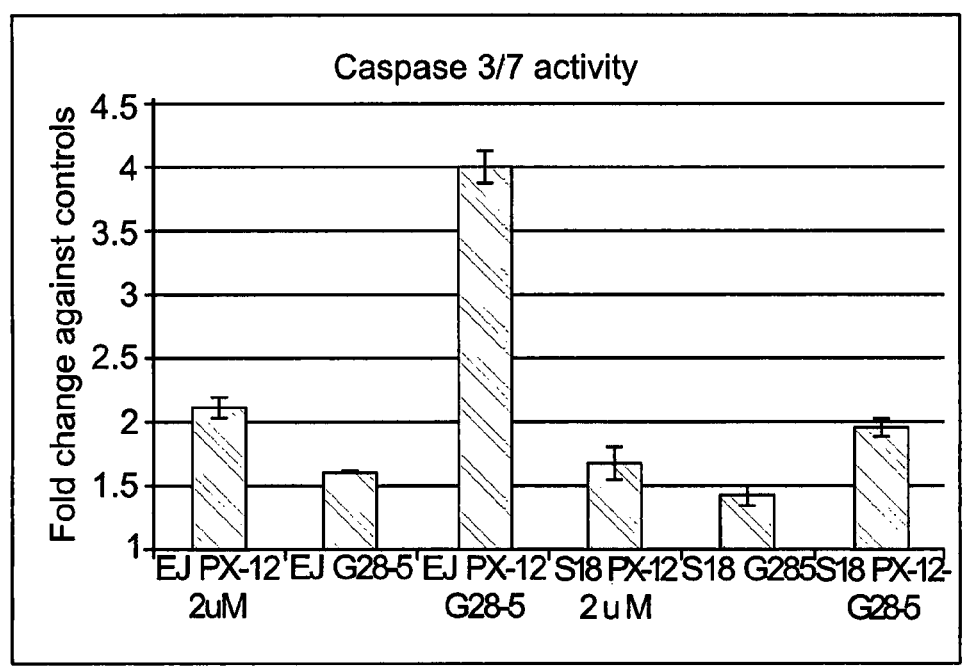
FIG. 7 shows a graph comparing apoptosis in bladder cancer EJ cells and ASK-1 protein knock-out derivatives ('S18') treated with soluble CD40 agonist (agonistic antibody G28-5), the indicated concentration of Trx inhibitor (PX-12), or their combination.

FIG. 7 shows the comparison of bladder cancer EJ cells and ASK-1 protein knock-out derivatives ('S18') that were treated with soluble CD40 agonist (agonistic antibody G28-5), the indicated concentration of Trx inhibitor (PX-12), or their combination. Apoptosis was assessed on the basis of caspase activity detection after 24 hours of treatment using the Sensolyte (Anaspec) assay (Cambridge Biosciences).

It can be seen that the combination therapy (soluble agonist G28-5 and Trx inhibitor PX-12) induce cell death in EJ cells. Also, the loss of ASK-1 in EJ cells (S18 cells) results in abrogation of apoptosis, which was assessed by caspase detection.

The results demonstrate that the ROS-ASK1 signalling pathway is essential for the induction of apoptosis by mCD40L and also by the combinatorial Trx/TNF agonist therapy. This provides evidence that the combinatorial therapy is not only equally efficient at inducing death in carcinoma cells but also engages the same signalling pathways in cells.

Figure 8:
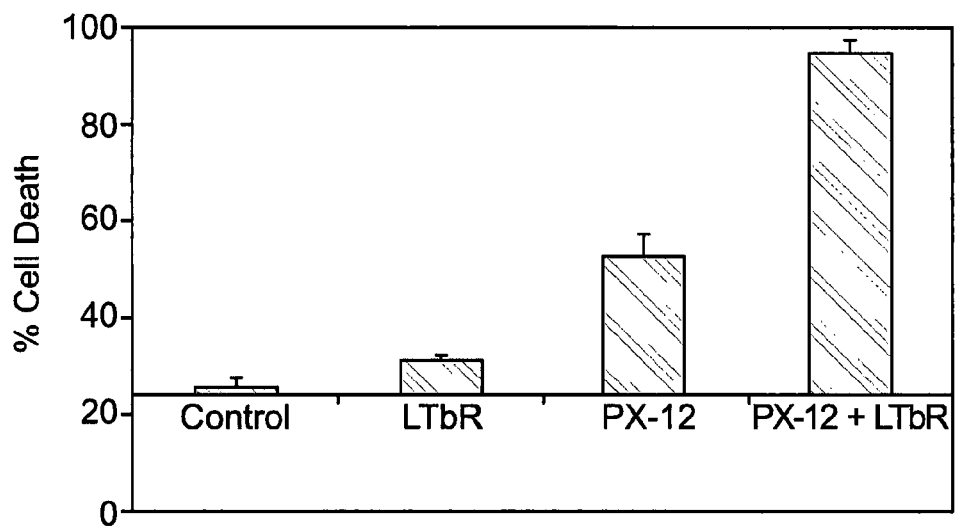
FIG. 8 shows a graph comparing colorectal carcinoma SW480 cells treated with 5 microg/mL of Lymphotoxin beta receptor (LTbR) agonist (humanized tetravalent LTBR agonistic antibody BS-1), 4 microM of Trx inhibitor (PX-12), and their combination.

Turning to FIG. 8 which shows the results (% Cell Death) of colorectal carcinoma SW480 cells were treated with 5 microg/mL of Lymphotoxin beta receptor (LTbR) agonist (humanized tetravalent LTBR agonistic antibody BS-1, supplied by Biogen Idec Inc), 4 microM of Trx inhibitor (PX-12), and their combination. Apoptosis was assessed 12 hours later using the Cytotox-Glo assay (Promega). Results were obtained as relative luciferase activity in comparison to negative controls and subsequently percentage (%) cell death values were deduced for each condition according to the manufacturer's instructions. Results are representative of two independent experiments in which six technical replicates were carried out for each condition.

The results demonstrate that although the LTbR agonist alone shows little pro-apoptotic activity on carcinoma cells, and the Trx inhibitor alone shows some but not extensive cytotoxicity, the combinatorial Trx inhibitor/receptor agonist therapy is synergistically inducing rapid and extensive apoptosis in these cells. Moreover, the findings demonstrate that the efficacy of the combinatorial approach is not CD40-specific and the Trx inhibitor/TNFR agonist is affective for other members of the TNFR family.

Figure 9:
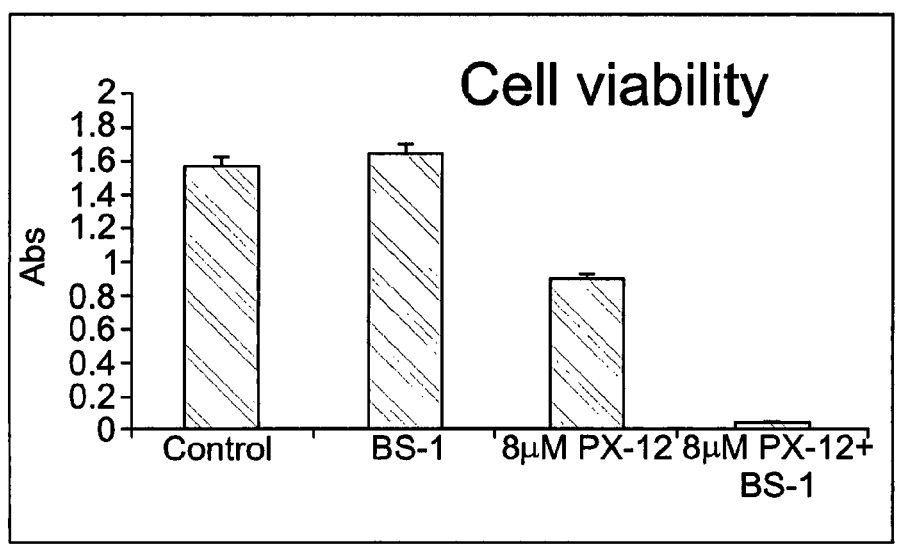
FIG. 9 shows a graph comparing graph comparing bladder carcinoma EJ cells treated with 25 microg/mL of Lymphotoxin beta receptor (LTbR) agonist (humanized tetravalent LTBR agonistic antibody BS-1), 8 microM of Trx inhibitor (PX-12), and their combination.
Figures 10A, 10B:
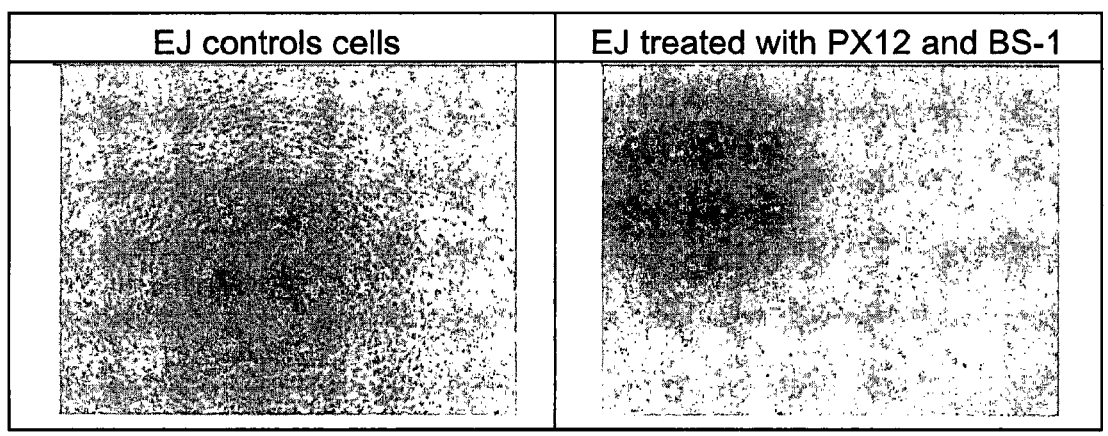
FIGS. 10a and 10b show the bladder carcinoma EJ cells with no treatment (control) and the combination of PX-12 with BS-1.

FIGS. 9 and 10 provide further evidence of the improved efficacy of the combinatorial approach whereby bladder carcinoma EJ cells cultured in 96 well plates were treated with 25 microg/mL of Lymphotoxin beta receptor (LTbR) agonist (humanized tetravalent LTBR agonistic antibody BS-1, supplied by Biogen Idec Inc), 8 microM of Trx inhibitor (PX-12), and their combination.

Cell viability was assessed 48 hours later using the Cell Titre Aqueous One Solution assay (Promega). Results are shown as Absorbance at 492 nm and values are representative of cell viability. Results are representative of two independent experiments in which six to eight technical replicates were carried out for each condition.

Cultures from representative experiments performed as above were assessed by phase contrast microscopy and images were taken at ×100 magnification to qualitatively confirm loss of viability and visible signs of cell death in control and treated cells. These results can be seen in FIG. 10.

The results are in agreement with findings in FIG. 8, and demonstrate that although the LTbR agonist alone shows little pro-apoptotic activity on carcinoma cells, the combinatorial Trx inhibitor/receptor agonist therapy is synergistically inducing extensive apoptosis in these cells. The findings confirm the efficacy of the combinatorial approach for other members of the TNFR family (apart from CD40) and in particular LTbR and also that different types of cancer cells are highly susceptible (i.e. bladder and colorectal).

The invention claimed is:

1. A composition for the treatment of cancerous cells, wherein said composition includes a combination of at least one tumor necrosis factor receptor agonist and at least one thioredoxin inhibitor, wherein inhibition of thioredoxin is by direct inhibition;
and wherein the thioredoxin inhibitor includes any one or any combination of 2-[(1-Methylpropyl)dithio]-1H-imidazole (PX-12), PMX464, or analogues of the aforementioned.

2. A composition according to claim 1 wherein the tumor necrosis factor receptor agonist is soluble in aqueous media and/or bulk phase solutions.

3. A composition according to claim 1 wherein the tumor necrosis factor receptor agonist is a ligand for one or more tumor necrosis factor receptors.

4. A composition according to claim 1 wherein the tumor necrosis factor receptor agonist is an agonist to a non-classical death domain tumor necrosis factor.

5. A composition according to claim 1 wherein the tumor necrosis factor receptor agonist is any one or any combination of recombinant soluble trimeric ligands, recombinant soluble multimeric ligands, agonistic tumor necrosis factor receptor antibodies (alone or cross-linked using appropriate immunoglobulins), cell surface-presented or membrane-presented tumor necrosis factor receptor agonists, tumor necrosis factor receptor agonists on nanoparticles, tumor necrosis factor receptor ligands delivered by viral expression vectors.

6. A composition according to claim 1 wherein the tumor necrosis factor receptor agonist is at least one lymphotoxin beta receptor (LTbR) agonist.

7. A composition according to claim 1 wherein the thioredoxin inhibitor is a redox inhibitor.

8. A composition according to claim 1 wherein the thioredoxin inhibitor is an inhibitor of the thioredoxin-1 pathway.

* * * * *